US00PP29615P3

(12) United States Plant Patent
Van Swieten

(10) Patent No.: US PP29,615 P3
(45) Date of Patent: Aug. 21, 2018

(54) ***PHALAENOPSIS* ORCHID PLANT NAMED 'PHALFEQBIN'**

(50) Latin Name: ***Phalaenopsis* hybrid**
Varietal Denomination: PHALFEQBIN

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 28 days.

(21) Appl. No.: 15/530,070

(22) Filed: Nov. 30, 2016

(65) Prior Publication Data

US 2018/0153077 P1 May 31, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFEQBIN', particularly characterized by having small, white flowers with dark purple spots, 1 to 3 peduncles that are medium long and sturdy, leaves that are narrow oblong, and is propagated by meristem tissue culture, is disclosed.

3 Drawing Sheets

Genus and species: *Phalaenopsis* hybrid.
Variety denomination: 'PHALFEQBIN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFEQBIN'.

The new *Phalaenopsis* plant is a product of a planned breeding program conducted by the inventor in Bleiswijk, The Netherlands. The objective of this breeding program was to create a new *Phalaenopsis* plant with small, white flowers with dark purple spots suitable for potted plant production.

The new *Phalaenopsis* plant 'PHALFEQBIN' is a result of cross-pollination made by the inventor in July 2007 in Bleiswijk, The Netherlands of the proprietary female, or seed parent, *Phalaenopsis* hybrid '17746-03' (unpatented) with the proprietary male, or pollen parent, *Phalaenopsis* hybrid '01-2077' (unpatented).

The new *Phalaenopsis* was selected by the inventor as a single plant within the progeny of the stated cross-pollination in a controlled greenhouse in Bleiswijk, The Netherlands in July 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALFEQBIN' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFEQBIN' as a new and distinct variety of *Phalaenopsis* plant.

1) Small, white flowers with dark purple spots;
2) 1 to 3 peduncles;
3) Peduncle is medium long and sturdy; and
4) Shape of the leaf is narrow oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in October 2016. Colors in the photographs may differ from the color values cited in the detailed botanical description, which accurately describe the actual colors of the new variety.

DESCRIPTION OF THE NEW VARIETY

Figure 1:
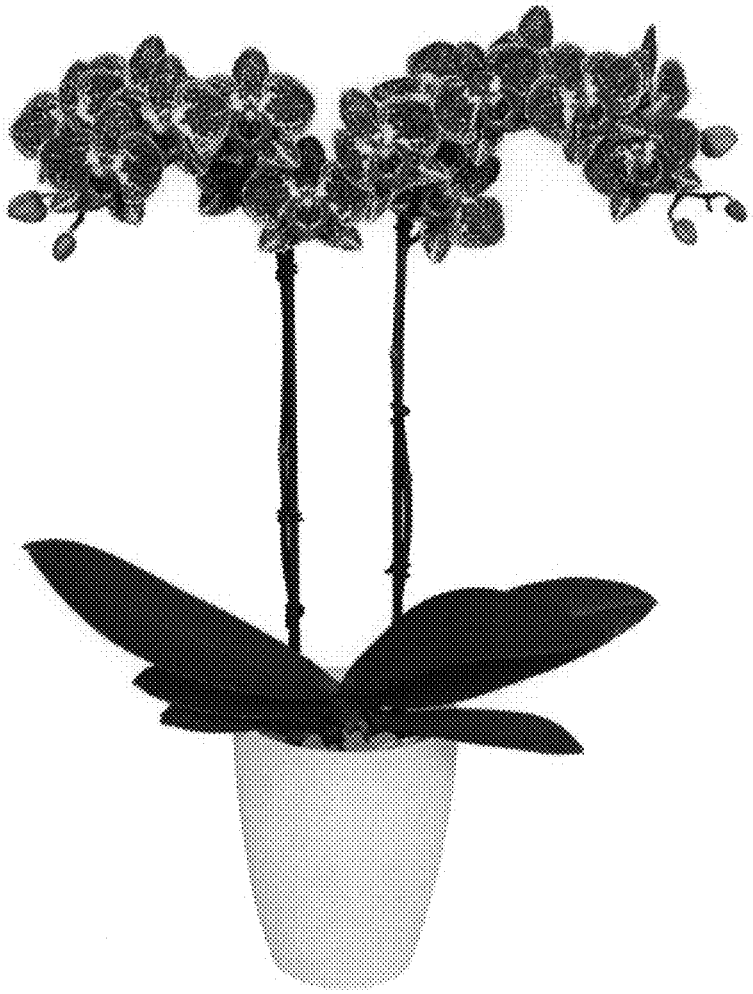
FIG. 1 shows the overall plant habit, including blooms, buds and foliage of 'PHALFEQBIN'.
Figure 2:
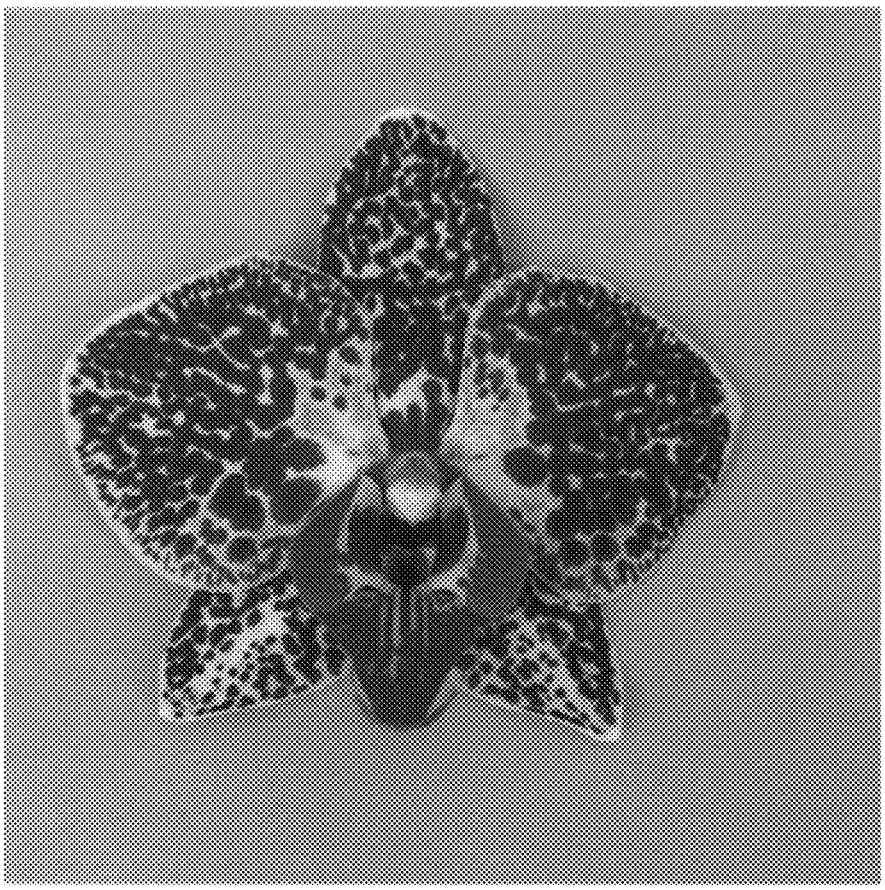
FIG. 2 shows a close-up of a flower of 'PHALFEQBIN'.
Figure 3:
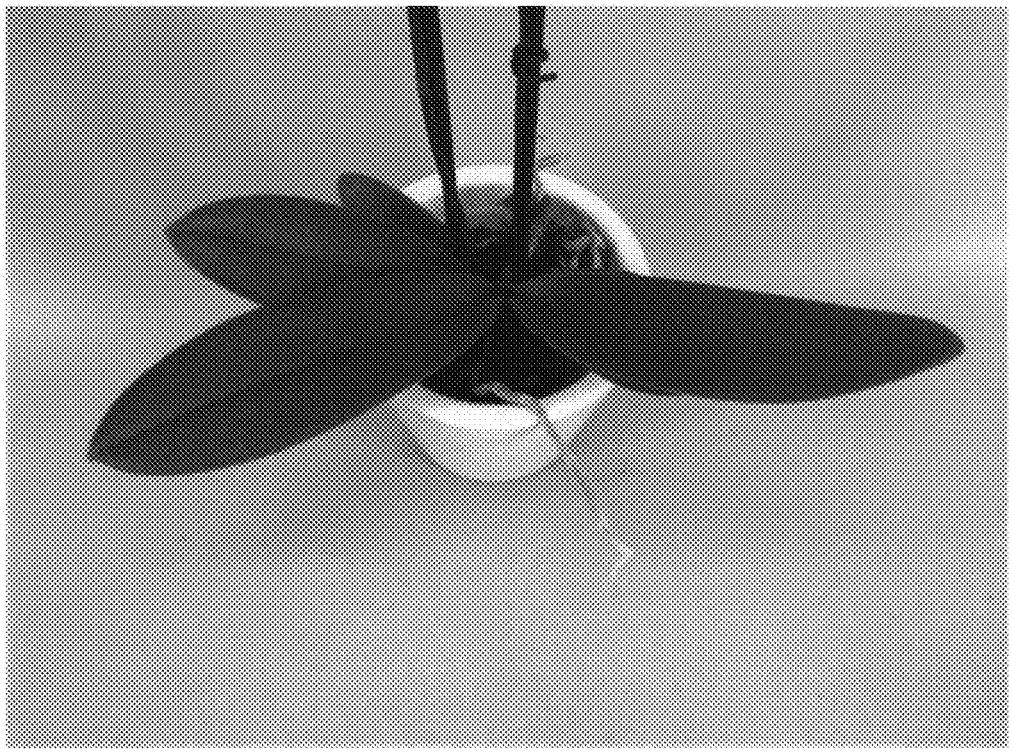
FIG. 3 shows a close-up of the leaves of 'PHALFEQBIN'.

The following detailed description sets forth the distinctive characteristics of 'PHALFEQBIN'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in October 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFEQBIN'.

Parentage:

*Female parent*.—*Phalaenopsis* cultivar '17746-03' (unpatented).

*Male parent*.—*Phalaenopsis* cultivar '01-2077' (unpatented).

Propagation:

*Type*.—Meristem tissue culture.

Roots:

*Root description*.—Greyed-green (RHS 190B/C) colored roots with green (RHS 144B) and purple (RHS N77A/B) colored root tips. (The exact shades of the roots may vary with minimal changes of environmental conditions, such as root moisture and location inside or outside of the pot).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 34.0 cm to 44.0 cm.

*Width* (*measured from leaf tips*).—About 32.0 cm to 37.0 cm.

*Vigor*.—Strong.

Leaves:

*Mature leaves*.—Quantity per plant: 7 to 10 leaves are produced before flowering. Length (fully expanded): 17.0 cm to 19.0 cm. Width: 5.0 cm to 6.0 cm. Shape: Narrow oblong. Base shape: Moderately elongated. Apex: Unequal obtuse. Leaf blade angle with the petiole (measured from the horizontal position): Between 5 degrees and 15 degrees. Leaf margin: Entire. Color: Upper surface: RHS 146A. Lower surface: RHS 146B. Texture: Upper surface: Rough. Lower surface: Smooth. Thickness: 2.4 mm to 2.6 mm. Variegation: Absent. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—10 to 15.

*Length*.—41.0 cm to 46.0 cm.

*Diameter*.—3.7 mm to 3.9 mm.

*Strength*.—Strong.

*Aspect*.—Upright.

*Texture*.—Smooth.

*Color*.—Brown (RHS 200B) with a touch of green (RHS 146B).

*Internode length*.—45.0 mm to 55.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Number of inflorescences*.—1 to 3.

*Inflorescence size*.—Height (from base to tip): 220.0 mm to 240.0 mm.

*Flowering time*.—First flowers can be expected 10 to 11 months after planting in a 12 cm (diameter) pot.

*Flower*.—Height: 53.0 mm to 58.0 mm. Diameter: 58.0 mm to 63.0 mm. Depth of lip: 16.0 mm to 18.0 mm.

*Flower longevity*.—On the plant: 15 to 22 weeks.

*Fragrance*.—Absent.

*Flower bud*.—Length: 15.0 mm to 17.0 mm. Width: 14.0 mm to 16.0 mm. Shape: Egg shaped. Color: Green (RHS 146B) and purple on the top (RHS NN78C) with diluted dark purple spots (RHS N79B).

*Petals*.—Arrangement: Open/free. Shape: Semi-circular. Apex: Obtuse asymmetric. Margin: Entire. Length (from base to tip): 27.0 mm to 29.0 mm. Width: 30.0 mm to 32.0 mm. Position of broadest part of petal: At the base. Color (when fully opened): Upper surface: Basic color: White (RHS NN155C). Over color: Light purple (RHS N75B) and dark purple spots (RHS N79B). Lower surface: Basic color: White (RHS NN155C). Over color: Light purple (RHS 76C) and diluted dark purple spots (RHS N79B).

*Dorsal sepal*.—Shape: Elliptic. Apex: Obtuse asymmetric. Margin: Entire. Length (from base to tip): 30.0 mm to 32.0 mm. Width: 17.0 mm to 19.0 mm. Color (when fully opened): Upper surface: Basic color: White (RHS NN155C). Over color: Slightly light purple (RHS N75B) and dark purple spots (RHS N79B). Lower surface: Basic color: Light purple (RHS 76C). Over color: Light purple (RHS 76A) towards the apex and diluted dark purple spots (RHS N79B).

*Lateral sepals*.—Shape: Ovate. Apex: Obtuse asymmetric. Margin: Entire. Length (from base to tip): 31.0 mm to 33.0 mm. Width: 17.0 mm to 19.0 mm. Color (when fully opened): Upper surface: Basic color: White (RHS NN155C). Over color: Light purple (RHS N75B) and dark purple spots (RHS N79B). Lower surface: Basic color: Light purple (RHS 76C). Over color: Purple stripe (RHS N75B) in the middle towards the apex and diluted dark purple spots (RHS N79B).

*Labellum* (*lip*).—Whiskers: Present. Length of whiskers: 11.0 mm to 13.0 mm. Color of whiskers: Purple (RHS N79B/C) spotted (RHS NN155C). Pubescence on the lip: Absent.

*Lateral lobe*.—Shape: Spatulate. Margin: Entire. Length (from base to tip): 15.0 mm to 17.0 mm. Width: 11.0 mm to 13.0 mm. Color: White (RHS NN155C) at the base; purple (RHS N78A) and yellow (RHS 13A) on one side; spotted and two stripes (RHS 183B).

*Apical lobe*.—Shape: Triangular. Margin: Entire. Length: 16.0 mm to 18.0 mm. Width: 17.0 mm to 19.0 mm. Color: Yellow (RHS 13A) at the base; purple (RHS N79C) towards the whiskers; red-purple (RHS 59B) spots.

*Callus*.—Average size: Small. Height: 0.4 cm to 0.5 cm. Length: 0.4 cm to 0.5 cm. Width: 0.2 cm to 0.3 cm. Color: Dark purple (RHS 187A) with yellow tips (RHS 9A); white (RHS NN155C) on the sides.

*Reproductive organs*.—Column: Length: 7.0 mm to 9.0 mm. Diameter: 4.5 mm to 4.7 mm. Color: Purple (RHS N78B). Pollinia: Quantity: 2. Diameter: 1.0 mm to 1.2 mm. Color: Yellow-orange (RHS N25B). Ovary: Length: 9.0 mm to 11.0 mm. Diameter: 2.0 mm to 2.2 mm. Pedicel: Length: 32.0 mm to 34.0 mm. Diameter: 2.3 mm to 2.5 mm. Color: Green (RHS 145B/C) at the base; light purple (RHS 76C) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALFEQBIN' differs from female parent plant '17746-03' (unpatented) in that 'PHALFEQBIN' has a spotted flower pattern and an obtuse asymmetric petal apex, whereas '17746-03' has a striped flower pattern and a rounded petal apex. Additionally, 'PHALFEQBIN' has smaller flowers and a shorter plant height than '17746-03'.

'PHALFEQBIN' differs from male parent plant '01-2077' (unpatented) in that 'PHALFEQBIN' has a spotted flower pattern and an obtuse asymmetric petal apex, whereas '01-2077' has a flecked flower pattern and an obtuse petal apex. Additionally, 'PHALFEQBIN' has larger flowers and a taller plant height than '01-2077'.

'PHALFEQBIN' is most similar to the commercial *Phalaenopsis* plants named 'PHALDONFI' (U.S. Plant Pat. No. 26,066) and 'PHALDIMAN' (unpatented). 'PHALFEQBIN' differs from the commercial variety 'PHALDONFI' in that 'PHALFEQBIN' has a dark purple callus with yellow tips and flowers with a white basic color and a spotted pattern, whereas 'PHALFIMWAQ' has a yellow dotted callus and flowers with a light pink basic color and a striped pattern. Additionally, 'PHALFEQBIN' has larger flowers and longer whiskers than 'PHALDONFI'.

'PHALFEQBIN' differs from the commercial variety 'PHALDIMAN' in that 'PHALFEQBIN' has a triangular apical lobe, a dark purple callus with yellow tips and flowers with a white basic color and a spotted pattern, whereas 'PHALDIMAN' has an elliptic apical lobe, a dark purple callus and flowers with a light yellow basic color and an edged pattern. Additionally, 'PHALFEQBIN' has larger flowers and longer whiskers than 'PHALDIMAN'.

I claim:

1. A new and distinct variety of *Phalaenopsis* plant named 'PHALFEQBIN', substantially as described and illustrated herein.

* * * * *